United States Patent [19]

Kraatz et al.

[11] Patent Number: 4,742,071
[45] Date of Patent: May 3, 1988

[54] NOVEL 2-ARYL-2-AZOLYLMETHYL-1,3-DIOXEPINE FUNGICIDES

[75] Inventors: Udo Kraatz; Gerhard Jäger, both of Leverkusen; Karl H. Büchel, Burscheid; Wilhelm Brandes, Leichlingen; Paul Reinecke, Leverkusen; Hans-Dieter Scharf, Roetgen; Herbert Frauenrath, Aachen, all of Fed. Rep. of Germany

[73] Assignee: Bayer Aktiengesellschaft, Leverkusen, Fed. Rep. of Germany

[21] Appl. No.: 759,018

[22] Filed: Jul. 25, 1985

Related U.S. Application Data

[62] Division of Ser. No. 522,939, Aug. 12, 1983, Pat. No. 4,559,355.

[30] Foreign Application Priority Data

Sep. 3, 1982 [DE] Fed. Rep. of Germany ....... 3232737

[51] Int. Cl.$^4$ ................. C07D 249/08; C07D 233/54; A61K 31/41; A61K 31/415
[52] U.S. Cl. .................... 514/383; 514/184; 514/397; 548/101; 548/262; 548/336
[58] Field of Search ............... 549/347; 548/262, 101, 548/336; 514/383, 397, 450

[56] References Cited

U.S. PATENT DOCUMENTS

| 3,575,999 | 4/1971 | Godefrai et al. | 548/336 |
| 4,160,838 | 7/1979 | Van Reet et al. | 548/262 |

FOREIGN PATENT DOCUMENTS

| 0029355 | 5/1981 | European Pat. Off. | 548/336 |
| 2551560 | 5/1976 | Fed. Rep. of Germany | 548/262 |
| 2027701 | 2/1980 | United Kingdom | 548/262 |

Primary Examiner—Richard L. Raymond
Assistant Examiner—D. L. Dinner
Attorney, Agent, or Firm—Sprung Horn Kramer & Woods

[57] ABSTRACT

2-Aryl-2-azolylmethyl-1,3-dioxepines of the formula $$\begin{array}{c} Ar\diagdown\phantom{C}\diagup CH_2-Az \\ \phantom{Ar\diagdown}C \\ O\diagup\phantom{C}\diagdown O \\ \diagdown_X\diagup \end{array}$$

in which
Az is imidazol-1-yl or 1,2,4-triazol-1-yl,
X is the ethylene or vinylene grouping, and
Ar is optionally substituted aryl, or addition products thereof with acids or metal salts, which possess fungicidal activity.

20 Claims, No Drawings

NOVEL 2-ARYL-2-AZOLYLMETHYL-1,3-DIOXEPINE FUNGICIDES

This is a division of application Ser. No. 522,939, filed Aug. 12, 1983, now U.S. Pat. No. 4,559,355.

The invention relates to new 2-aryl-2-azolylmethyl-1,3-dioxepines, a process for their preparation and their use as plant protection agents.

It has already been disclosed that certain azolylmethyl-ketals, such as, for example, 2-(2,4-dichlorophenyl)-4-n-propyl-2-(1,2,4-triazol-1-yl-methyl)-1,3-dioxolane or 2-(2,4-dichlorophenyl)-4-methyl-2-(1,2,4-triazol-1-yl-methyl)-1,3-dioxolane (compare DE-OS (German Published Specification) 2,551,560), or certain azolylmethyl-carbinols, such as, for example, (1,2,4-triazol-1-yl-methyl)-(4-chlorophenyl)-carbinol (compare U.S. Ser. No. 792 756, filed May 2, 1977), have fungicidal properties.

However, the action of these compounds is not always completely satisfactory, especially when low amounts and concentrations are used.

New 2-aryl-2-azolylmethyl-1,3-dioxepines of the general formula (I)

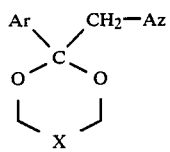

in which
Az represents imidazol-1-yl or 1,2,4-triazol-1-yl,
X represents the ethylene or vinylene grouping and
Ar represents optionally substituted aryl,
and acid addition salts and metal salt complexes thereof which are tolerated by plants, have been found.

It has furthermore been found that the new 2-aryl-2-azolylmethyl-1,3-dioxepines of the general formula (I) are obtained by a process in which the corresponding 2-aryl-2-halogenomethyl-1,3-dioxepines of the formula (II)

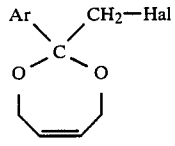

in which
Ar represents optionally substituted aryl and
Hal represents halogen,
are reacted with alkali metal salts of azoles of the formula (III)

$$Az-M \quad \text{(III)}$$ 

in which
Az has the abovementioned meaning and
M represents an alkali metal,
in the presence of a diluent, to give the compounds of the formula (Ia) according to the invention

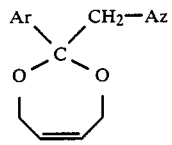

in which
Ar and Az have the abovementioned meaning (formula (Ia) corresponds to formula (I), but X in (I) represents the vinylene group);
if desired, these can be catalytically hydrogenated with hydrogen in the presence of a catalyst and if appropriate in the presence of a diluent to give the compounds of the formula (Ib) according to the invention

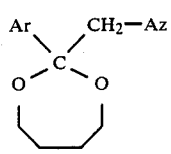

in which
Ar and Az have the abovementioned meaning (formula (Ib) corresponds to formula (I), but in this case X in (I) represents the ethylene group).

If desired, an acid or a metal salt can then be added onto the compounds of the formula (Ia) or (Ib) thus obtained.

The new 2-aryl-2-azolylmethyl-1,3-dioxepines of the formula (I) have powerful fungicidal properties. Surprisingly, the compounds according to the invention exhibit a better fungicidal activity than the compounds 2-(2,4-dichlorophenyl)-4-n-propyl-2-(1,2,4-triazol-1-yl-methyl)-1,3-dioxolane, 2-(2,4-dichlorophenyl)-4-methyl-2-(1,2,4-triazol-1-yl-methyl)-1,3-dioxolane or (1,2,4-triazol-1-yl-methyl)-(4-chloropnenyl)-carbinol, which are known from the prior art and are closely related compounds chemically and from the point of view of their action.

The substances according to the invention thus represent an enrichment of the prior art.

Formula (I) provides a general definition of the 2-aryl-2-azolylmethyl-1,3-dioxepines according to the invention.

Preferred compounds of the formula (I) are those in which
Az and X have the meaning given in the definition of the invention and
Ar represents optionally substituted phenyl, particularly suitable substituents being: halogen, cyano, nitro, alkyl, alkoxy and alkylthio with in each case 1 to 4 carbon atoms, halogenoalkyl, halogenoalkoxy and halogenoalkylthio with in each case 1 or 2 carbon atoms and 1 to 5 halogen atoms, dialkylamino, alkoxycarbonyl, alkoxycarbonylamino and N-alkyl-alkoxycarbonylamino with in each case 1 to 4 carbon atoms in the particular alkyl parts, and phenyl and phenoxy which are optionally substituted by halogen or alkyl with 1 to 4 carbon atoms.

Very particularly preferred compounds of the formula (I) are those in which
Az and X have the meaning given in the definition of the invention and
Ar represents phenyl which is optionally mono-, di- or tri-substituted by identical or different substituents, very particularly preferred substituents being: fluorine, chlorine, bromine, cyano, nitro, methyl, methoxy, methylthio, methoxycarbonyl, trifluoromethyl, trifluoromethoxy, trifluoromethylthio, ethyl, ethoxy, ethoxycarbonyl, dimethylamino, acetamido and N-methylacetamido, and phenyl and phenoxy which are optionally mono-, di- or tri-substituted by identical or different radicals from the group comprising fluorine, chlorine and methyl.

If, for example, 2-bromomethyl-2-(4-chlorophenyl)-1,3-2H-4,7-dihydrodioxepine and the sodium salt of imidazole are used as starting substances, the course of the reaction can be represented by the following equation:

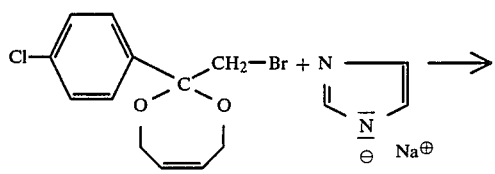

If, for example, 2-(4-chlorophenyl)-2-(imidazol-1-yl-methyl)-1,3-2H-4,7-dihydrodioxepine is used as the starting substance and hydrogen is used as the hydrogenating agent, the course of the reaction can be represented by the following equation:

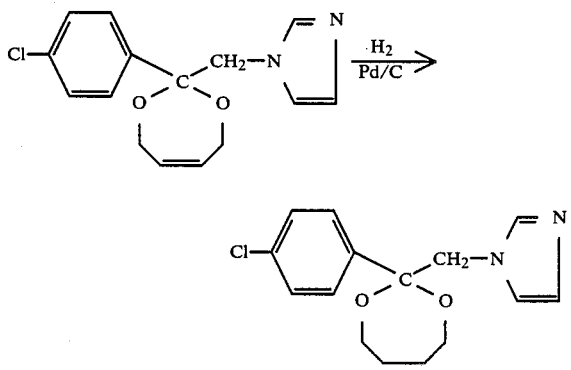

Formula (II) provides a general definition of the 2-aryl-2-halogenomethyl-1,3-dioxepines required as starting substances in carrying out the process according to the invention.

In this formula (II), Ar preferably has the same meaning as has been mentioned as preferred for this substituent in the description of the substances of the formula (I) according to the invention. Hal preferably represents chlorine or bromine.

The 2-aryl-2-halogenomethyl-1,3-dioxepines of the formula (II) are not yet known. They are obtained by a process in which the corresponding aracyl halides of the general formula (IV)

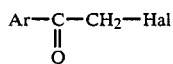

in which
Ar and Hal have the abovementioned meaning,
are first ketalized with trimethyl orthoformate or acetone dimethyl acetal in the presence of a diluent, such as, for example, methanol, and in the presence of an acid catalyst, such as, for example, p-toluenesulfonic acid, at temperatures between 40° C. and 100° C., and, in a second stage, the resulting dimethyl ketals of the formula (V)

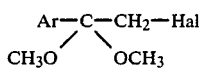

in which
Ar and Hal have the abovementioned meaning,
are trans-ketalized with 2-butene-1,4-diol in the presence of an acid catalyst, such as, for example, p-toluenesulfonic acid, at temperatures between 20° C. and 80° C., if appropriate under reduced pressure.

The aracyl halides of the formula (IV) are known (compare J. Amer. Chem. Soc. 52, 818 (1930); U.S. Pat. No. 3,936,470; and Zh. Obshch. Khim. 33, 1,135 (1963)).

Formula (III) provides a general definition of the alkali metal salts of azoles which are also to be used as starting substances for the process according to the invention. In this formula, Az preferably has the meaning given in the general definition of the invention. M preferably represents sodium or potassium.

The alkali metal salts of azoles, of the formula (III), are generally known. They are obtained by reacting imidazole or 1,2,4-triazole with sodium methylate or potassium methylate, or by reacting imidazole or triazole with the equivalent amount of a corresponding alkali metal hydride.

Possible diluents for the process according to the invention are inert organic solvents. These include, preferably, amides, such as dimethylformamide, dimethylacetamide or N-methylacetanilide, and furthermore dimethylsulphoxide and hexamethylphosphoric acid triamide.

Possible diluents for the hydrogenation of the substances (Ia) according to the invention to give the substances (Ib) according to the invention are likewise inert organic solvents. These include, preferably, aliphatic or aromatic hydrocarbons, such as benzine, benzene, toluene or xylene; halogenated hydrocarbons, such as methylene chloride, chloroform, carbon tetrachloride or chlorobenzene; ethers, such as diethyl ether, dioxane or tetrahydrofuran; esters, such as ethyl acetate; and alcohols, such as methanol, ethanol or isopropanol.

All the customary hydrogenation catalysts can be used in carrying out the hydrogenation of the substances (Ia) according to the invention to give the substances (Ib) according to the invention. Preferably, noble metal catalysts, such as, for example, platinum or palladium, if desired on a suitable support, such as, for example, charcoal, are used.

The reaction temperatures can be varied within a substantial range in carrying out the process according to the invention. In general, the reaction is carried out between +20° C. and +180° C., preferably between +60° C. and +150° C.

The reaction temperature in the hydrogenation of the substances (Ia) according to the invention to give the substances (Ib) according to the invention can likewise be varied within a substantial range. In general, the reaction is carried out between +10° C. and +200° C., preferably between +20° C. and +100° C.

The hydrogenation of the substances (Ia) according to the invention to give the substances (Ib) according to the invention can be carried out under increased pressure. In general, the reaction is carried out in the pressure ranges between 1 and 10 atmospheres, preferably between 4 and 6 atmospheres.

In carrying out the process according to the invention, 1 to 2 mols of the azole-alkali metal salt of the formula (III) are preferably used per mol of the compound of the formula (II). The compounds of the formula (Ia) are isolated by customary methods.

In carrying out the hydrogenation of the substances (Ia) according to the invention to give the substances (Ib) according to the invention, 1 to 5 g, preferably 2 to 3 g, of hydrogenation catalyst are added per 0.1 mol of compound of the formula (Ia). The hydrogenation and working up and the isolation of the compounds of the formula (Ib) are carried out by customary methods.

The following acids can preferably be used for the preparation of physiologically acceptable acid addition salts of the compounds of the formula (I): hydrogen halide acids, such as, for example, hydrochloric acid and hydrobromic acid, and furthermore phosphoric acid, nitric acid, sulphuric acid, monofunctional and bifunctional carboxylic acids and hydroxycarboxylic acids, such as, for example, acetic acid, maleic acid, succinic acid, fumaric acid, tartaric acid, citric acid, salicylic acid, sorbic acid and lactic acid, and sulphonic acids, such as, for example, p-toluenesulphonic acid and 1,5-naphthalenesulphonic acid.

The acid addition salts of the compounds of the formula (I) can be obtained in a simple manner by customary salt formation methods, such as, for example, by dissolving a compound of the formula (I) in a suitable inert solvent and adding the acid, such as, for example, hydrogen chloride, and they can be isolated in a known manner, for example by filtration, and if necessary purified by washing with an inert organic solvent.

Salts of metals of main groups II to IV and of subgroups I and II and IV to VIII are preferably used for the preparation of metal salt complexes of the compounds of the formula (I), examples of metals which may be mentioned being copper, zinc, manganese, magnesium, tin, iron and nickel.

Possible anions of the salts are those which are preferably derived from the following acids: hydrogen halide acids, such as, for example, hydrochloric acid and hydrobromic acid, and furthermore phosphoric acid, nitric acid and sulphuric acid.

The metal salt complexes of the compounds of the formula (I) can be obtained in a simple manner by customary processes, thus, for example, by dissolving the metal salt in alcohol, for example ethanol, and adding the solution to the compound of the formula (I). The metal salt complexes can be isolated in a known manner, for example by filtration, and if appropriate purified by recrystallization.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants, of the active compounds, at the concentrations required for combating plant diseases, permits treatment of above-ground parts of plants, of vegetative propagation stock and seeds, and of the soil.

As plant protection agents, the active compounds according to the invention can be used with particularly good success for combating Venturia species, such as, for example, against the apple scab causative organism (*Ventura inequalis*), Erysiphe species, such as, for example, against the powdery mildew of cereal causative organism (*Erysiphe graminis*) or Sphaerotheca species, such as, for example, against the powdery mildew of cucumber causative organism (*Sphaerotheca fuliginea*). In addition, the compounds according to the invention also exhibit a good action against the cereal diseases rust, *Septoria nodorum*, *Cochliobolus sativus* and *Pyrenophora teres*, and against the rice diseases *Pyricularia oryzae* and *Pellicularia sasakii*.

When applied in relatively high amounts, the substances according to the invention also exhibit a selective herbicidal action and a growth-regulating action.

The active compounds can be converted to the customary formulations, such as solutions, emulsions, wettable powders, suspensions, powders, dusting agents, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysation products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, bactericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02% by weight, are required at the place of action.

PREPARATION EXAMPLES

Example 1

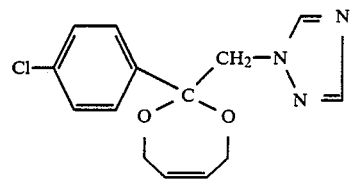

6 g (0.2 mol) of 80% pure sodium hydride are added in portions to 14 g (0.2 mol) of 1,2,4-triazole in 100 ml of dimethylformamide at 20° to 25° C. After 10 minutes, 30.1 g (0.1 mol) of 2-bromomethyl-2-(4-chlorophenyl)-1,2-2H-4,7-dihydrodioxepine in 75 ml of dimethylformamide are added dropwise and the mixture is stirred at 140° C. for 8 hours. Most of the dimethylformamide is distilled off in vacuo and the residue is taken up in water. The mixture is extracted three times with methylene chloride and the combined methylene chloride extracts are washed with water and concentrated in vacuo, and filtered over a short silica gel column for purification. After the solvent has been evaporated off, 21 g (72% of theory) of 2-(4-chlorophenyl)-2-(1,2,4-triazol-1-yl-methyl)-1,3-2H-4,7-dihydrodioxepine of melting point 100° C. are obtained.

Example 2

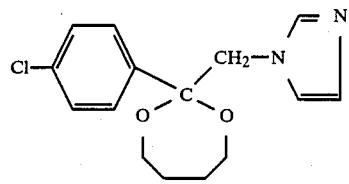

25 g (0.09 mol) of 2-(4-chlorophenyl)-2-(1,2,4-imidazol-1-yl-methyl)-1,3-2H-4,7-dihydrodioxepine are dissolved in 300 ml of ethyl acetate and are hydrogenated with 3 g of palladium-on-charcoal under 4 to 6 atmospheres and at 20° C.-25° C. When the uptake of hydrogen has ended, the catalyst is filtered off and the solvent is removed from the filtrate in vacuo. The oily residue crystallizes when stirred with cyclohexane. After the crystals have been filtered off with suction and dried, 19 g (75% of theory) of 2-(4-chlorophenyl)-2-(1,2,4-imidazol-1-yl-methyl)-1,3-perhydrodioxepine of melting point 65° C. to 68° C. are obtained.

The following compounds of the general formula (I)

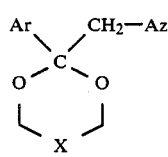

(I)

can be obtained according to Examples 1 and 2 and according to the process conditions described.

| Example No. | Ar | Az | X | Melting point (°C.) |
|---|---|---|---|---|
| 3 | 4-Cl-C6H4- | imidazol-1-yl | -CH=CH- | 151 |
| 4 | 2,4-Cl2-C6H3- | 1,2,4-triazol-1-yl | -CH=CH- | 82 |
| 5 | 2,4-Cl2-C6H3- | imidazol-1-yl | -CH=CH- | 107 |
| 6 | 4-C6H5-C6H4- | 1,2,4-triazol-1-yl | -CH=CH- | 129 |
| 7 | 4-C6H5-C6H4- | imidazol-1-yl | -CH=CH- | 130 |
| 8 | 4-Cl-C6H4- | 1,2,4-triazol-1-yl | -CH2-CH2- | 85 |
| 9 | 2,4-Cl2-C6H3- | 1,2,4-triazol-1-yl | -CH2-CH2- | 60 |
| 10 | 2,4-Cl2-C6H3- | imidazol-1-yl | -CH2-CH2- | 55-60 |
| 11 | 4-C6H5-C6H4- | 1,2,4-triazol-1-yl | -CH2-CH2- | 97 |
| 12 | 4-C6H5-C6H4- | imidazol-1-yl | -CH2-CH2- | 97 |

Preparation of the Starting Substances of the Formula (II):

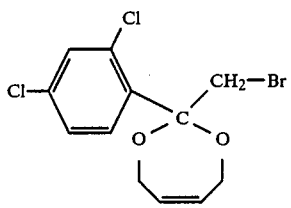
(II-1)

666.6 g (2.1 mols) of 2,4-dichlorophenacyl bromide dimethyl ketal are mixed with 1 liter of 2-butene-1,4-diol and 2 g of paratoluenesulphonic acid in a distillation apparatus, and the mixture is warmed at 40° C. under a waterpump vacuum for 12 hours, while stirring. After the reaction mixture has been cooled, it is partitioned between 1.5 liters of ether and 2 liters of saturated potassium carbonate solution, the organic phase is separated off and, after the solvent has been evaporated off, the oily residue is distilled. 326 g (46% of theory) of 2-bromomethyl-2-(2,4-dichlorophenyl)-1,3-2H-4,7-dihydrodioxepine of boiling point Bp$_{0.25}$: 150° C. are obtained.

The following starting substances of the general formula (II):

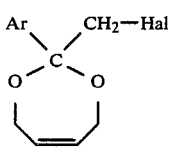
(II)

are obtained analogously.

| Example No. | Ar | Hal | Melting Point(°C.) |
|---|---|---|---|
| (II-2) | Cl—⟨phenyl⟩— | Br | 74 |
| (II-3) | C$_6$H$_5$—⟨phenyl⟩— | Br | 107 |

Preparation of the Intermediates of the Formula (V):

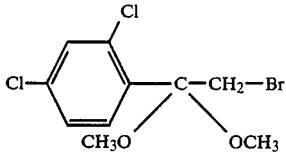
(V-1)

420 g (1.6 mols) of 2,4-dichlorophenacyl bromide are dissolved in 500 ml of methanol with 340 g (3.2 mols) of trimethyl orthoformate and 5 g of paratoluenesulphonic acid, and the solution is boiled under reflux for 12 hours. A further 100 g of ortho-ester and 2 g of paratoluenesulphonic acid are then added and the mixture is heated under reflux for another 10 hours. After cooling, the reaction mixture is poured into saturated potassium carbonate solution and the product is extracted with several portions of methylene chloride. The combined methylene chloride phases are washed with water and dried over sodium sulphate and the solvent is removed in vacuo. The oily residue is distilled. 337 g (67% of theory) of 2,4-dichlorophenacyl bromide dimethyl ketal of boiling point Bp$_{0.15}$: 135° C. are thus obtained.

The following intermediates of the general formula (V):

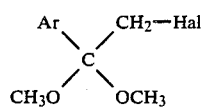
(V)

are obtained in an analogous manner.

| Example No. | Ar | Hal | Melting Point (°C.) |
|---|---|---|---|
| (V-2) | Cl—⟨phenyl⟩— | Br | 50 |
| (V-3) | C$_6$H$_5$—⟨phenyl⟩— | Br | 94 |

USE EXAMPLES

The compounds shown here are used as comparison substances in the Use Examples which follow:

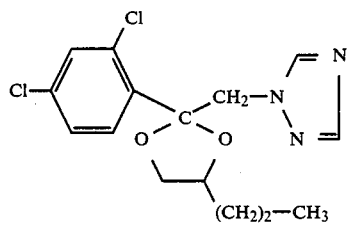
(A)

2-(2,4-Dichlorophenyl)-4-n-propyl-2-(1,2,4-triazol-1-yl-methyl)-1,3-dioxolane

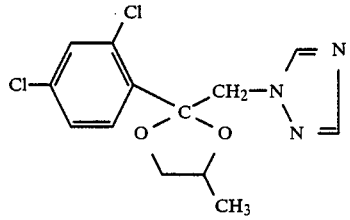
(B)

2-(2,4-Dichlorophenyl)-4-methyl-2-(1,2,4-triazol-1-yl-methyl)-1,3-dioxolane

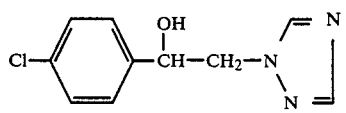
(C)

4-Chlorophenyl-(1,2,4-triazol-1-yl-methyl)-carbinol

Example A

Sphaerotheca test (cucumber)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are dusted with conidia of the fungus *Sphaerotheca fuliginea*.

The plants are then placed in a greenhouse at 23° to 24° C. and at a relative atmospheric humidity of about 75%.

Evaluation is carried out 10 days after the inoculation.

In this test, a clearly superior activity compared with the prior art is shown, for example, by the compounds according to the following preparation examples: (4) and (9).

Example B

Venturia test (apple)/protective
Solvent: 4.7 parts by weight of acetone
Emulsifier: 0.3 parts by weight of alkylaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous conidia suspension of the apple scab causative organism (*Venturia inaequalis*) and then remain in an incubation cabinet at 20° C. and 100% relative atmospheric humidity for 1 day.

The plants are then placed in a greenhouse at 20° C. and a relative atmospheric humidity of about 70%.

Evaluation is carried out 12 days after the inoculation.

In this test, a clearly superior activity compared with the prior art is shown, for example, by the compounds according to the following preparation example: (9).

Example C

Erysiphe test (barley)/protective
Solvent: 100 parts by weight of dimethylformamide
Emulsifier: 0.25 parts by weight of alkaryl polyglycol ether To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are dusted with spores of *Erysiphe graminis* f. sp. hordei.

The plants are placed in a greenhouse at a temperature of about 20° C. and a relative atmospheric humidity of about 80%, in order to promote the development of powdery mildew pustules.

Evaluation is carried out 7 days after the inoculation.

In this test, a clearly superior activity compared with the prior art is shown, for example, by the compounds according to the following preparation examples: (1), (3), (4), (5), (6), (2), (8), (11) and (12).

Example D

Erysiphe test (barley)/seed treatment

The active compounds are used as dry dressings. These are prepared by extending the particular active compound with a ground mineral to give a finely pulverulent mixture, which ensures uniform distribution on the seed surface.

To apply the dressing, the seed is shaken with the dressing in a closed glass flask for 3 minutes.

3 batches of 12 grains of the barley are sown 2 cm deep in standard soil. 7 days after sowing, when the young plants have unfolded their first leaf, they are dusted with spores of *Erysiphe graminis* f. s. hordei.

The plants are placed in a greenhouse at a temperature of about 20° C. and a relative atmospheric humidity of about 80% in order to promote the development of powdery mildew pustules.

Evaluation is carried out 7 days after the inoculation.

In this test, a clearly superior activity compared with the prior art is shown, for example, by the compounds according to the following preparation examples: (4) and (5).

It will be understood that the specification and examples are illustrative but not limitative of the present invention and that other embodiments within the spirit and scope of the invention will suggest themselves to those skilled in the art.

What is claimed is:

1. A 1-aryl-2-azolylmethyl-1,3-dioxepine of the formula

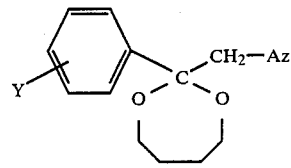

in which
Az is imidazolyl-1-yl or 1,2,4-triazol-1-yl, and
Y at least once is chlorine, or phenyl which is optionally substituted by halogen or alkyl with 1 to 4 carbon atoms,
or an addition product thereof with an acid or metal salt.

2. A compound or addition product according to claim 1, in which
Y is from one to three substituents independently selected from the group consisting of chlorine, and phenyl which is optionally substituted up to three times by substituents independently selected from the group comprising fluorine, chlorine and methyl.

3. A compound according to claim 1, wherein such compound is 2-(4-biphenylyl)-2-(1,2,4-triazol-1-yl-methyl)-1,3-perhydrodioxepine of the formula

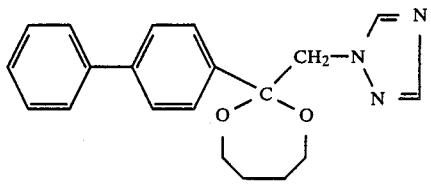

or an addition product thereof with an acid or metal salt.

4. A fungicidal composition comprising a fungicidally effective amount of a compound or addition product according to claim 1 in admixture with a diluent.

5. A method combating fungi which comprises administering to such fungi or to a fungus habitat a fungicidally effective amount of a compound or addition product according to claim 1.

6. A method combating fungi which comprises administering to such fungi or to a fungus habitat a fungicidally effective amount of a compound or addition product according to claim 3.

7. A 2-aryl-2-imidazolylmethyl-1,3-dioxepine of the formula

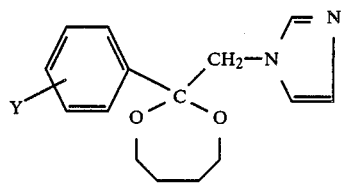

in which
Y is chlorine, or phenyl which is optionally substituted by halogen or alkyl with 1 to 4 carbon atoms, or an addition product thereof with an acid or metal salt.

8. A compound or addition product according to claim 7, in which
Y is hydrogen, chlorine, or phenyl which is optionally substituted up to three times by substituents independently selected from the group comprising fluorine, chlorine and methyl.

9. A compound according to claim 7, wherein such compound is 2-(4-biphenylyl)-2-(imidazol-1-yl-methyl)-1,3-perhydrodioxepine of the formula

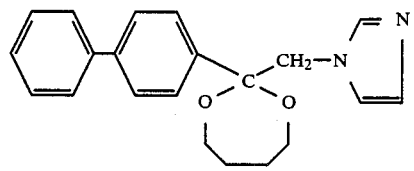

or an addition product thereof with an acid or metal salt.

10. A fungicidal composition comprising a fungicidally effective amount of a compound or addition product according to claim 7 in admixture with a diluent.

11. A method combating fungi which comprises administering to such fungi or to a fungus habitat a fungicidally effective amount of a compound or addition product according to claim 7.

12. A method combating fungi which comprises administering to such fungi or to a fungus habitat a fungicidally effective amount of a compound or addition product according to claim 9.

13. A 2-aryl-2-azolylmethyl-1,3-perhydrodioxepine of the formula

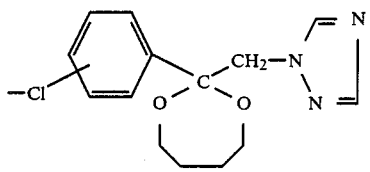

or an addition product thereof with an acid or metal salt.

14. A fungicidal composition comprising a fungicidally effective amount of a compound or addition product according to claim 13 in admixture with a diluent.

15. A method of combating fungi which comprises administering to such fungi or to a fungus habitat a fungicidally effective amount of a compound or addition product according to claim 13.

16. The method according to claim 15, wherein such compound is
2-(4-biphenylyl)-2-(1,2,4-triazol-1-yl-methyl)-1,3-2H-4,7-dihydrodioxepine,
2-(2,4-dichlorophenyl)-2-(1,2,4-triazol-1-yl-methyl)-1,3-perhydrodioxepine,
2-(2,4-dichlorophenyl)-2-(imidazol-1-yl-methyl)-1,3-perhydrodioxepine, or
2-(4-chlorophenyl)-2-(1,2,4-triazol-1-yl-methyl)-1,3-perhydrodioxepine,
or an addition product thereof with an acid or metal salt.

17. A compound or addition product according to claim 1, in which
Y is from one to three substituents independently selected from the group consisting of chlorine, and phenyl optionally substituted up to three times by substituents independently selected from the group comprising fluorine, chlorine and methyl.

18. A fungicidal composition comprising a fungicidally effective amount of a compound or addition product according to claim 1 in admixture with a diluent.

19. A compound according to claim 13, wherein such compound is 2-(4-chlorophenyl)-2-(1,2,4-triazol-1-yl-methyl)-1,3-perhydrodioxepine of the formula

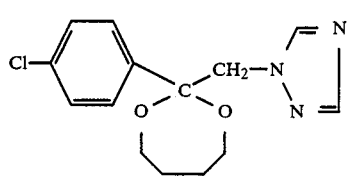

or an addition product thereof with an acid or metal salt.

20. A compound according to claim 13, wherein such compound is 2-(2,4-dichlorophenyl)-2-(1,2,4-triazol-1-yl-methyl)-1,3-perhydrodioxepine of the formula

17
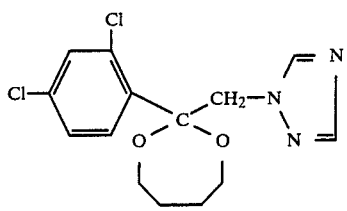
or an addition product thereof with an acid or metal salt.
* * * * *
18
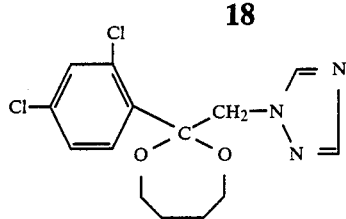
or an addition product thereof with an acid or metal salt.
* * * * *